(12) United States Patent
Sasaki et al.

(10) Patent No.: US 7,257,436 B2
(45) Date of Patent: Aug. 14, 2007

(54) APPARATUS FOR GENERATING RADIATION APPLICATION SYNCHRONIZING SIGNAL

(75) Inventors: Takeshi Sasaki, Isesaki (JP); Hidenori Tashiro, Shinagawa-ku (JP); Yosuke Tamuro, Toda (JP)

(73) Assignee: Anzai Medical Kabushiki Kaisha, Tokyo (JP)

( * ) Notice: Subject to any disclaimer, the term of this patent is extended or adjusted under 35 U.S.C. 154(b) by 490 days.

(21) Appl. No.: 10/454,609

(22) Filed: Jun. 5, 2003

(65) Prior Publication Data

US 2004/0030235 A1 Feb. 12, 2004

(30) Foreign Application Priority Data

Jun. 5, 2002 (JP) ............................. 2002-163828

(51) Int. Cl.
*A61B 5/05* (2006.01)
(52) U.S. Cl. ....................... 600/428; 600/407
(58) Field of Classification Search ........ 600/407–428; 128/204.23
See application file for complete search history.

(56) References Cited

U.S. PATENT DOCUMENTS

| | | | |
|---|---|---|---|
| 2,967,944 A | | 1/1961 | Lusted |
| 4,387,722 A | | 6/1983 | Kearns |
| 5,067,494 A | | 11/1991 | Rienmueller et al. |
| 5,209,233 A | | 5/1993 | Holland et al. |
| 5,271,055 A | * | 12/1993 | Hsieh et al. ................. 378/95 |
| 5,363,844 A | * | 11/1994 | Riederer et al. ............ 600/413 |
| 5,482,042 A | * | 1/1996 | Fujita ......................... 600/428 |
| 6,062,216 A | * | 5/2000 | Corn ....................... 128/204.23 |
| 6,118,847 A | * | 9/2000 | Hernandez-Guerra et al. ................. 378/65 |
| 6,195,408 B1 | * | 2/2001 | Acharya et al. ............... 378/8 |
| 6,421,552 B1 | * | 7/2002 | Hsieh ........................ 600/425 |
| 6,597,939 B1 | * | 7/2003 | Lampotang et al. ........ 600/427 |
| 2001/0014772 A1 | * | 8/2001 | Lampotang et al. ........ 600/428 |
| 2002/0077534 A1 | * | 6/2002 | DuRousseau ............... 600/300 |

FOREIGN PATENT DOCUMENTS

| | | |
|---|---|---|
| DE | 3421 045 | 12/1985 |
| EP | 0 413 513 | 2/1991 |
| EP | 1 013 224 | 6/2000 |
| JP | 2-94511 | 7/1990 |
| JP | 7-23945 | 1/1995 |
| JP | 7-246245 | 9/1995 |
| JP | 8-276024 | 10/1996 |
| JP | 2000-175904 | 6/2000 |
| JP | 2000-201922 | 7/2000 |
| JP | 2000-262513 | 9/2000 |
| JP | 2001-346773 | 12/2001 |
| WO | WO99/42034 | 8/1999 |

* cited by examiner

*Primary Examiner*—Brian L. Casler
*Assistant Examiner*—Ashish Jasani
(74) *Attorney, Agent, or Firm*—Paul A. Guss (57) ABSTRACT

The level of a respiration signal obtained from a laser sensor or the like is indicated on a respiration monitor according to an output condition set by synchronizing signal output control device. While the level of the respiration signal is indicated on the respiration monitor, a synchronizing signal output device outputs a synchronizing signal according to the output condition and the respiration signal to an X-ray control device, which controls a high-voltage generating device to energize an X-ray source to apply X-rays to an examinee.

14 Claims, 11 Drawing Sheets

APPARATUS FOR GENERATING RADIATION APPLICATION SYNCHRONIZING SIGNAL

BACKGROUND OF THE INVENTION

1. Field of the Invention

The present invention relates to an apparatus for generating a synchronizing signal for applying a radiation to a respiratory moving object.

2. Description of the Related Art

In recent years, computer-assisted diagnosis apparatus such as CT (Computed Tomography) apparatus, CR (Computed Radiography) apparatus, MRI (Magnetic Resonance Imaging) apparatus have widely been used in the medical field.

For imaging the thoracic or abdominal region of an examinee to produce a highly accurate image, it is necessary to take into account the motion of organs in the body of the examinee caused by respiration of the examinee. Though it is customary to ask the examinee to stop its spontaneous breathing during the imaging period, the practice is often burdensome for the examinee. The examinee may possibly be a patient who is unable to stop breathing The above problems are not limited to the process of imaging examinees. When using radiotherapeutic apparatus, which applies radiation to an affected area of a patient for treatment, it can be difficult to direct radiation accurately if the affected area moves.

Various apparatuses have been proposed for detecting a motion of a respiratory moving object such as an examinee, predicting a position of the respiratory moving object from the detected motion, and applying radiation to the respiratory moving object at a timing based on the detected position. For example, Japanese laid-open patent publication No. 2000-262513 discloses an apparatus for generating X-rays within an exhaling period where the examinee has stable volume fluctuations based on an output signal from a respiratory sensor attached to the examinee, and collecting data from the examinee based on the X-rays applied. According to another apparatus disclosed in Japanese laid-open patent publication No. 7-246245, a synchronizing signal for applying radiation to an examinee is generated based on a signal which is detected by a pressure detector in contact with the body surface of the examinee or an air flow rate detector coupled to the mouth of the examinee.

The conventional apparatuses are capable of applying radiation to the examinee in view of the respiratory action of the examinee. However, the apparatus may not necessarily produce an optimum synchronizing signal because the respiration of the examinee varies widely depending on the age or the respiratory condition of the examinee, and the detected signal changes greatly depending on how the sensor for detecting the respiration is attached to the examinee. In order to generate an optimum synchronizing signal, it is necessary that the examinee or patient be forced to breathe stably. The attachment of the sensor and the adjustment of the sensor output signal must be done by a skilled operator.

SUMMARY OF THE INVENTION

It is a general object of the present invention to provide an apparatus which is capable of highly accurately generating a synchronizing signal for applying radiation with very simple settings.

A major object of the present invention is to provide an apparatus which is capable of generating a synchronizing signal by selecting an optimum one out of a plurality of moving object detectors.

Another object of the present invention is to provide an apparatus which is capable of generating an optimum synchronizing signal while assisting in adjusting a moving state of a respiratory moving object.

Still another object of the present invention is to provide an apparatus which is capable of generating a desired synchronizing signal based on an appropriate moving state signal which is obtained irrespective of the state of a moving state detector and a respiratory moving object.

Yet another object of the present invention is to provide an apparatus which is capable of generating a synchronizing signal and verifying an operating state of the apparatus using the generated synchronizing signal.

Yet still another object of the present invention is to provide an apparatus which is capable of generating a stable synchronizing signal by controlling a respiratory moving object.

A further object of the present invention is to provide an apparatus which is capable of generating an appropriate synchronizing signal by determining settings of a moving state detector with respect to a respiratory moving object.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
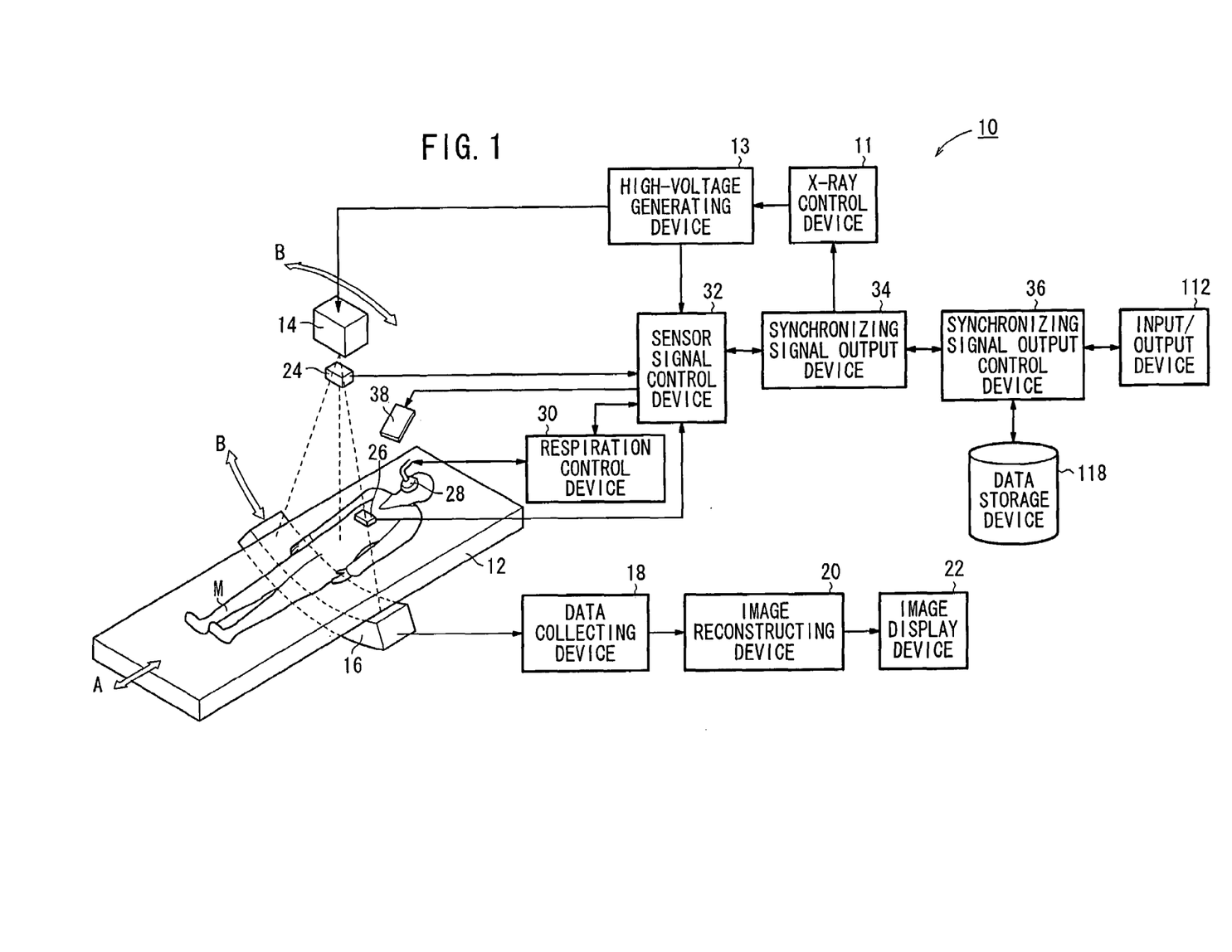
FIG. 1 is a schematic perspective view, partly in block form, of a radiation image capturing system to which a radiation application synchronizing signal generating apparatus according to an embodiment of the present invention is applied.

FIG. 1 shows, partly in block from, a radiation image capturing system 10 to which a radiation application synchronizing signal generating apparatus according to an embodiment of the present invention is applied.

As shown in FIG. 1, the radiation image capturing system 10 has an X-ray control device 11, a high-voltage generating device 13 for generating a high voltage according to a shot signal supplied from the X-ray control device 11, a bed 12 displaceable in the direction indicated by the arrow A with an examinee M (respiratory moving object) placed thereon, an X-ray source 14 for applying X-rays to the examinee M according to a high voltage supplied from the high-voltage generating device 13, an X-ray detector 16 for detecting X-rays that have passed through the examinee M, a data collecting device 18 for collecting examinee-transmitted data based on X-rays detected by the X-ray detector 16, an image reconstructing device 20 for reconstructing a tomographic image of the examinee M from examinee-transmitted data collected by the data collecting device 18, and an image display device 22 for displaying a reconstructed tomographic image on a CRT (Cathode Ray tube) or the like. The X-ray source 14 and the X-ray detector 16 are rotatable in the directions indicated by the arrow B. The components described above make up a CT (Computed Tomography) apparatus.

The radiation image capturing system 10 includes the radiation application synchronizing signal generating apparatus according to the embodiment of the present invention, which comprises a sensor signal control device 32 for producing a respiration signal (moving state signal) indicative of a respiratory state of the examinee M, a synchronizing signal output device 34 for outputting a synchronizing signal generated based on a respiration signal to the X-ray control device 11, and a synchronizing signal output control device 36 for controlling the timing to output a synchronizing signal.

To the sensor signal control device 32, there are connected a laser sensor 24 fixedly disposed above the examinee M for detecting a respiratory state of the examinee M as a distance signal, a load cell 26 disposed near the diaphragm or on the abdominal region of the examinee M for detecting a respiratory state of the examinee M as a pressure signal, and a respiration control device 30 coupled to a mask 28 attached to the mouth of the examinee M for controlling a respiratory state of the examinee M. The respiration control device 30 has a flow rate sensor for detecting a respiratory state of the examinee M as an air flow rate signal. The laser sensor 24, the load cell 26, and the respiration control device 30, each serving as a sensor, make up a moving state detector. The respiration control device 30 also serves as a moving state controller.

Figure 2:
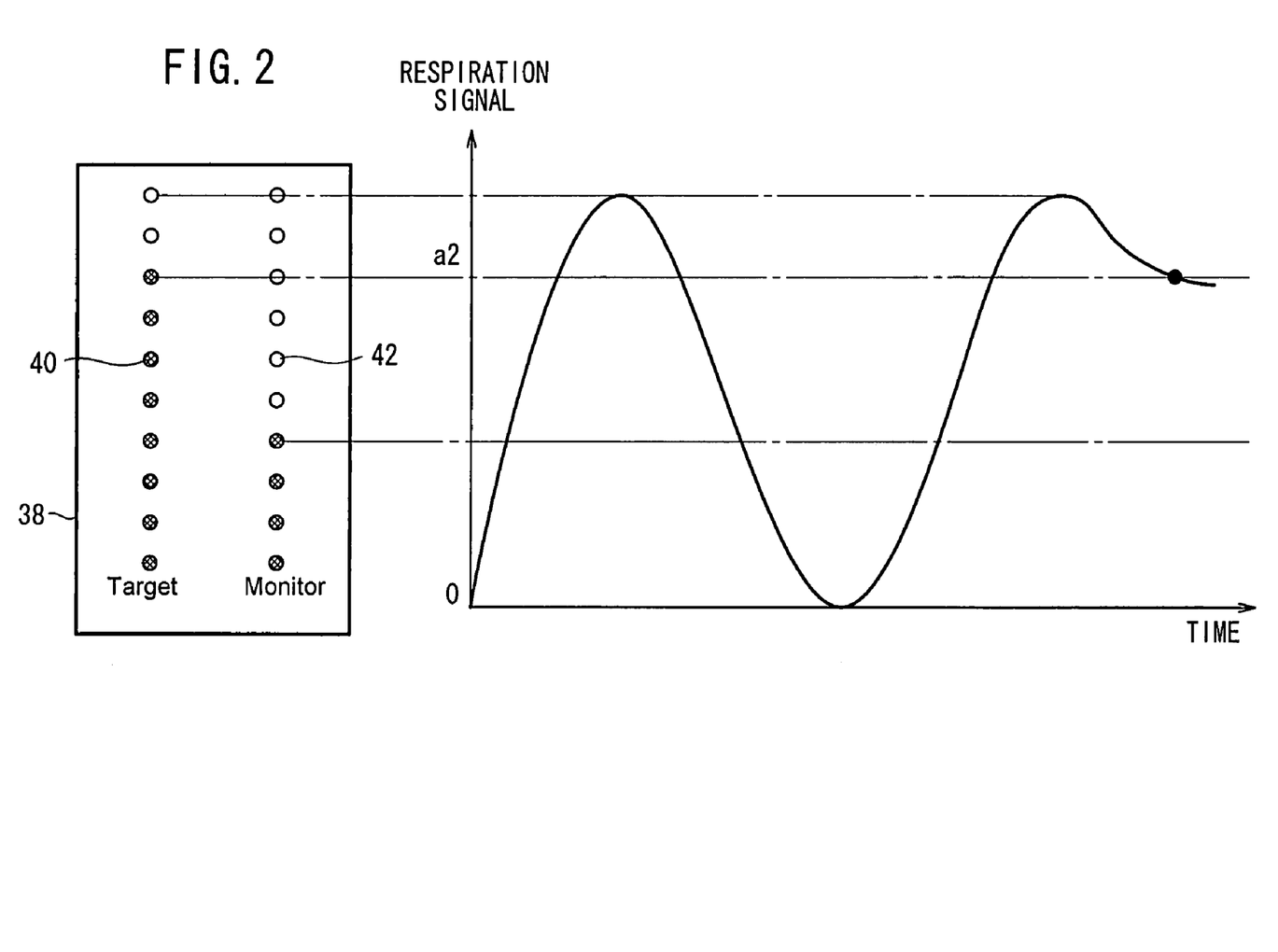
FIG. 2 is a diagram showing the relationship between a respiration monitor connected to a sensor signal control device of the radiation application synchronizing signal generating apparatus according to the embodiment of the present invention, and a respiration signal.

To the sensor signal control device 32, there is also connected a respiration monitor 38 (moving state indicator) that is positioned to be visually recognizable by the examinee M. As shown in FIG. 2, the respiration monitor 38 has a target respiration level indicator 40 for indicating a target respiration level, to be attained for imaging purpose, of the examinee M with 10 LEDs (Light Emitting Diodes) or the like, and a respiration level indicator 42 disposed parallel to the target respiration level indicator 40, for indicating a detected present respiration level of the examinee M with 10 LEDs or the like. Preferably, when the target respiration level indicator 40 and the respiration level indicator 42 are turned on, they should emit lights whose color can easily be confirmed by vision. For example, when turned on, the target respiration level indicator 40 may emit an orange light, and the respiration level indicator 42 may emit a green light.

Figure 3:
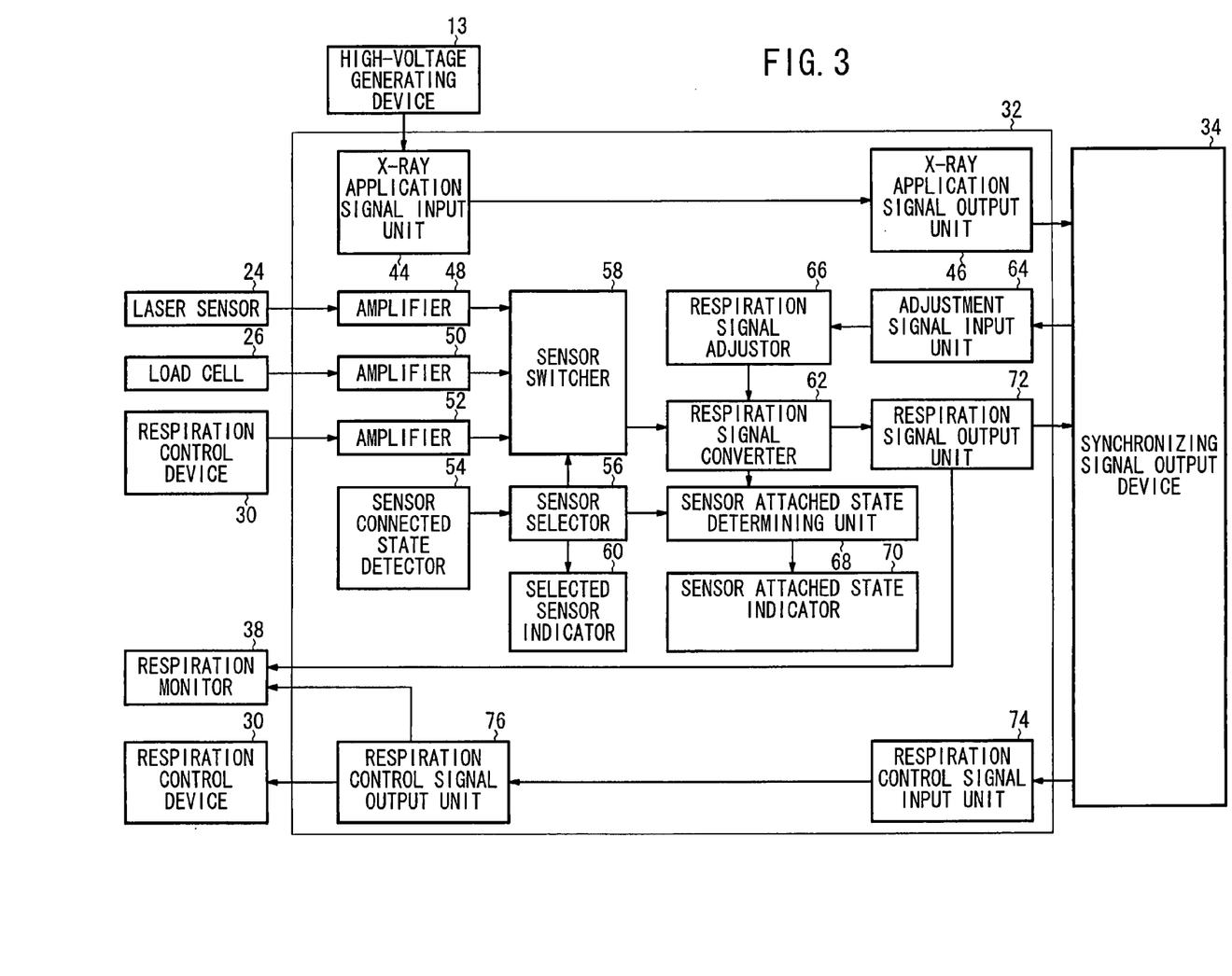
FIG. 3 is a block diagram of the sensor signal control device of the radiation application synchronizing signal generating apparatus according to the embodiment of the present invention.

FIG. 3 shows details of the sensor signal control device 32. As shown in FIG. 3, the sensor signal control device 32 has an X-ray application signal input unit 44 which is supplied from the high-voltage generating device 13 (applied state detector) with an X-ray application signal (applied state signal) that represents the supply of a high voltage from the high-voltage generating device 13 to the X-ray source 14 and the application of X-rays to the examinee M from the X-ray source 14, and an X-ray application signal output unit 46 which outputs the supplied X-ray application signal to the synchronizing signal output device 34.

The sensor signal control device 32 also has amplifiers 48, 50, 52 for amplifying a distance signal supplied from the laser sensor 24, a pressure signal supplied from the load cell 26, and an air flow rate signal supplied from the respiration control device 30, respectively, and a sensor connected state detector 54 (connected state detector) for detecting connected states of the laser sensor 24, the load cell 26, and the respiration control device 30 with respect to the sensor signal control device 32.

A sensor selector 56 (detector selector) for automatically selecting sensors according to a preset priority order is connected to the sensor connected state detector 54. The priority sequence may be set such that the respiration control device 30, the load cell 26, and the laser sensor 24 are selected in the order named. The sensor selector 56 controls a sensor switcher 58 for reading a signal from a selected sensor, and indicates the selected sensor on a selected sensor indicator 60 which comprises LEDs or the like.

To the sensor switcher 58, there is connected a respiration signal converter 62 for converting a respiration signal supplied from a sensor which has been selected by the sensor selector 56 into a predetermined level. A respiration signal adjustor 66 (moving state signal adjustor) for adjusting a respiration signal according to an adjustment signal supplied from the synchronizing signal output device 34 via an adjustment signal input unit 64 is connected to the respiration signal converter 62. The respiration signal adjustor 66 adjusts the amplitude and offset of a respiration signal that is supplied to the respiration signal converter 62 via the sensor switcher 58 to standardize the respiration signal, so as to be independent of the type of the sensor, the individual properties of the examinee M, and imaging conditions.

A sensor attached state determining unit 68 (set state determining unit) for determining a state in which the sensor is attached to the examinee M is connected to the respiration signal converter 62. The sensor attached state determining unit 68 determines a state in which the sensor is attached to the examinee M by comparing the level of a respiration signal with a predetermined decision level of the sensor, and indicates the result on a sensor attached state indicator 70. For example, the sensor attached state determining unit 68 determines whether the distance of the laser sensor 24 from the examinee M is too large, within an allowable range, or too small based on a respiration signal supplied from the laser sensor 24, and indicates the result by energizing the indicator lamps such as LEDs of the sensor attached state indicator 70. Alternatively, the sensor attached state determining unit 68 determines whether the attached state of the load cell 26 with respect to the examinee M is too strong, within an optimum range, or too weak, based on a respiration signal supplied from the load cell 26, and indicates the result on the sensor attached state indicator 70. The operator can adjust the attached state of the sensor based on the result indicated on the attached state indicator 70.

A respiration signal adjusted to an optimum range by the respiration signal converter 62 is supplied through a respiration signal output unit 72 to the synchronizing signal output device 34 and also to the respiration monitor 38 which is disposed near the examinee M. The respiration signal supplied to the respiration monitor 38 controls the energization of the respiration level indicator 42 shown in FIG. 2.

The sensor signal control device 32 also has a respiration control signal input unit 74 which is supplied with a respiration control signal from the synchronizing signal output device 34, and a respiration control signal output unit 76 for outputting a respiration control signal to the respiration monitor 38 and the respiration control device 30. The respiration control signal (target moving state signal) outputted to the respiration monitor 38 controls the energization of the target respiration level indicator 40, shown in FIG. 2, to indicate thereon a target respiration level of the examinee M to be attained for imaging purpose. The respiration control signal outputted to the respiration control device 30 enables the respiration control device 30 to impose a forced temporary stop on the respiration of the examinee M, cancel a forced temporary stop on the respiration of the examinee M, or supply necessary oxygen to the examinee M.

Figure 4:
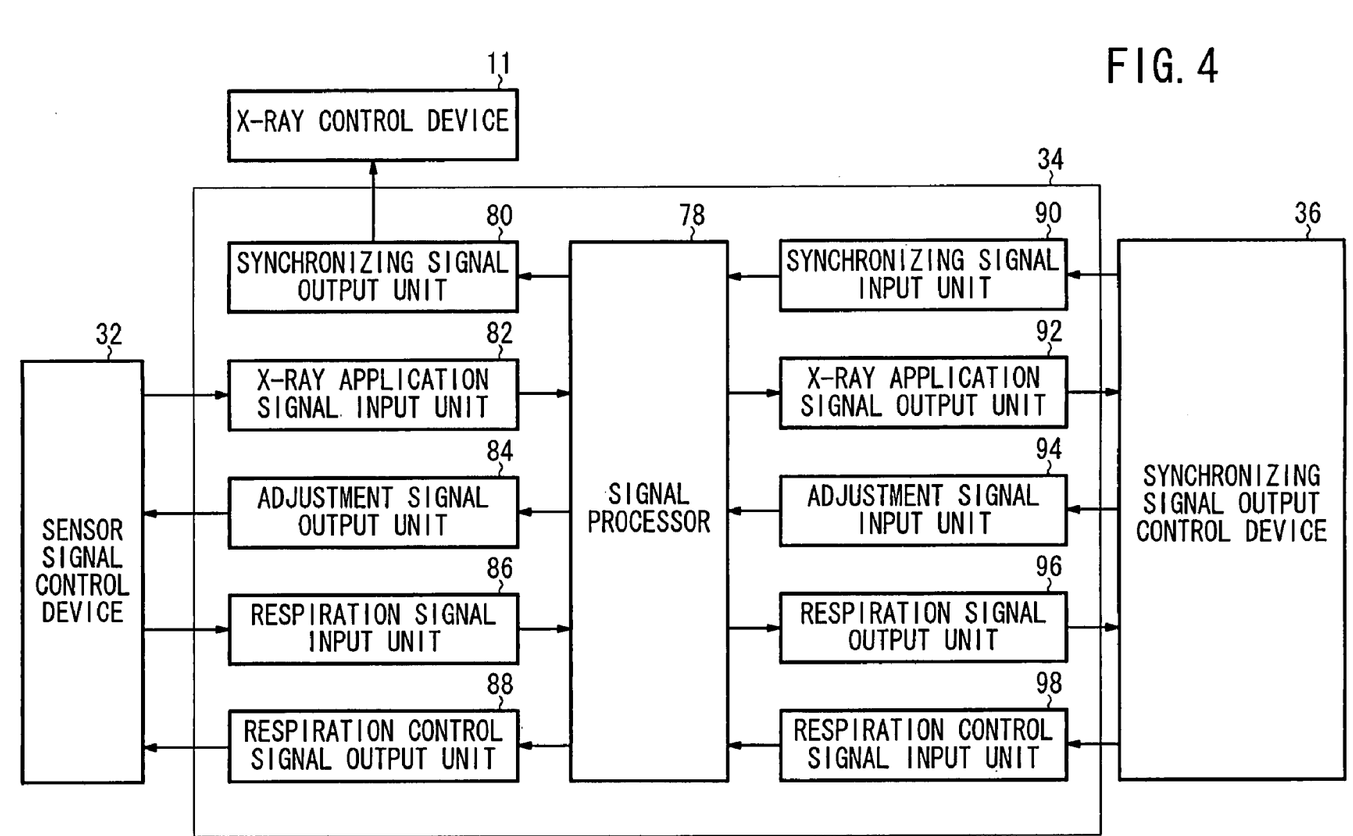
FIG. 4 is a block diagram of a synchronizing signal output device of the radiation application synchronizing signal generating apparatus according to the embodiment of the present invention.

FIG. 4 shows details of the synchronizing signal output device 34. As shown in FIG. 4, the synchronizing signal output device 34 has a signal processor 78 to which there are connected a synchronizing signal output unit 80 for outputting a synchronizing signal to the X-ray control device 11, an X-ray application signal input unit 82 for being supplied with an X-ray application signal from the sensor signal control device 32, an adjustment signal output unit 84 for outputting an adjustment signal to the sensor signal control device 32, a respiration signal input-unit 86 for being supplied with a respiration signal from the sensor signal control device 32, and a respiration control signal output unit 88 for outputting a respiration control signal to the sensor signal control device 32.

To the signal processor 78, there are also connected a synchronizing signal input unit 90 for being supplied with a synchronizing signal from the synchronizing signal output control device 36, an X-ray application signal output unit 92 for outputting an X-ray application signal to the synchronizing signal output control device 36, an adjustment signal input unit 94 for being supplied with an adjustment signal from the synchronizing signal output control device 36, a respiration signal output unit 96 for outputting a respiration signal to the synchronizing signal output control device 36, and a respiration control signal input unit 98 for being supplied with a respiration control signal from the synchronizing signal output control device 36.

The signal processor 78 (applied state determining unit) outputs a synchronizing signal supplied from the synchronizing signal output control device 36 to the X-ray control device 11 through the synchronizing signal output unit 80, and compares the synchronizing signal with an X-ray application signal generated by the high-voltage generating device 13 to determine whether X-rays are properly applied to the examinee M, and outputs the result to the X-ray control device 11. The signal processor 78 also calculates respiration phase data indicative of whether a respiration signal supplied from the sensor signal control device 32 represents an inhalation or an exhalation, and a maximum value of the respiration signal, and supplies the respiration phase data and the maximum value of the respiration signal to the synchronizing signal output control device 36.

Figure 5:
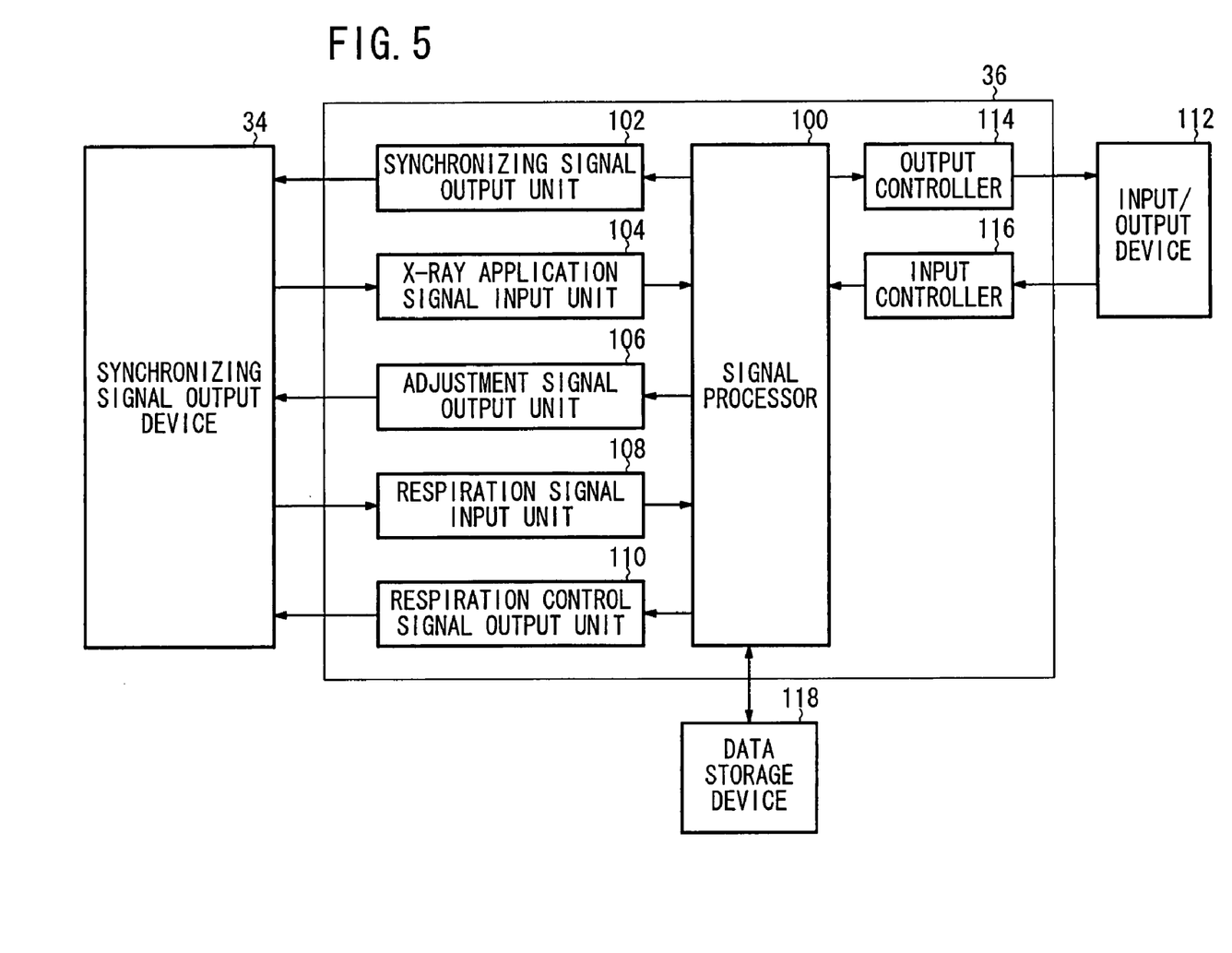
FIG. 5 is a block diagram of a synchronizing signal output control device of the radiation application synchronizing signal generating apparatus according to the embodiment of the present invention.

FIG. 5 shows details of the synchronizing signal output control device 36. As shown in FIG. 5, the synchronizing signal output control device 36 has a signal processor 100 to which there are connected a synchronizing signal output unit 102 for outputting a synchronizing signal to the synchronizing signal output device 34, an X-ray application signal input unit 104 for being supplied with an X-ray application signal from the synchronizing signal output device 34, an adjustment signal output unit 106 for outputting an adjustment signal to the sensor signal control device 32 through the synchronizing signal output device 34, a respiration signal input unit 108 for being supplied with a respiration signal from the synchronizing signal output device 34, and a respiration control signal output unit 110 for outputting a respiration control signal to the sensor signal control device 32 through the synchronizing signal output device 34.

To the signal processor 100, there are also connected an output controller 114 for controlling the outputting of display data to an input/output device 112 equipped with a CRT, a mouse, a keyboard, etc., an input controller 116 for controlling the inputting of command data supplied from the input/output device 112, and a data storage device 118 for storing various data that are acquired. The input/output device 112 displays the waveforms of a respiration signal, a synchronizing signal, and an X-ray application signal in real-time, and also displays operating states of the sensor signal control device 32, the synchronizing signal output device 34 and a connected state of the sensors.

The signal processor 100 (output condition setting unit, moving state signal determining unit, synchronizing signal generator) generates an adjustment signal for converting a respiration signal obtained from the examinee M into a predetermined level, and supplies the generated adjustment signal to the sensor signal control device 32 through the synchronizing signal output device 34. The signal processor 100 also tracks a respiration signal of the examinee M, and supplies a respiration control signal for controlling the respiration of the examinee M to the sensor signal control device 32 through the synchronizing signal output device 34. Furthermore, the signal processor 100 generates a synchronizing signal at a desired timing of a respiration signal supplied from the respiration signal input unit 108 according to a synchronizing signal output condition set by the operator. The signal processor 100 also controls the operation of the sensor signal control device 32 and the synchronizing signal output device 34, and monitors operating states of the sensor signal control device 32 and the synchronizing signal output device 34 and a connected state of the sensors.

The radiation image capturing system 10 according to the present embodiment is basically constructed as described above. Operation of the radiation image capturing system 10 will be described below with reference to a flowchart shown in FIG. 6.

Figure 6:
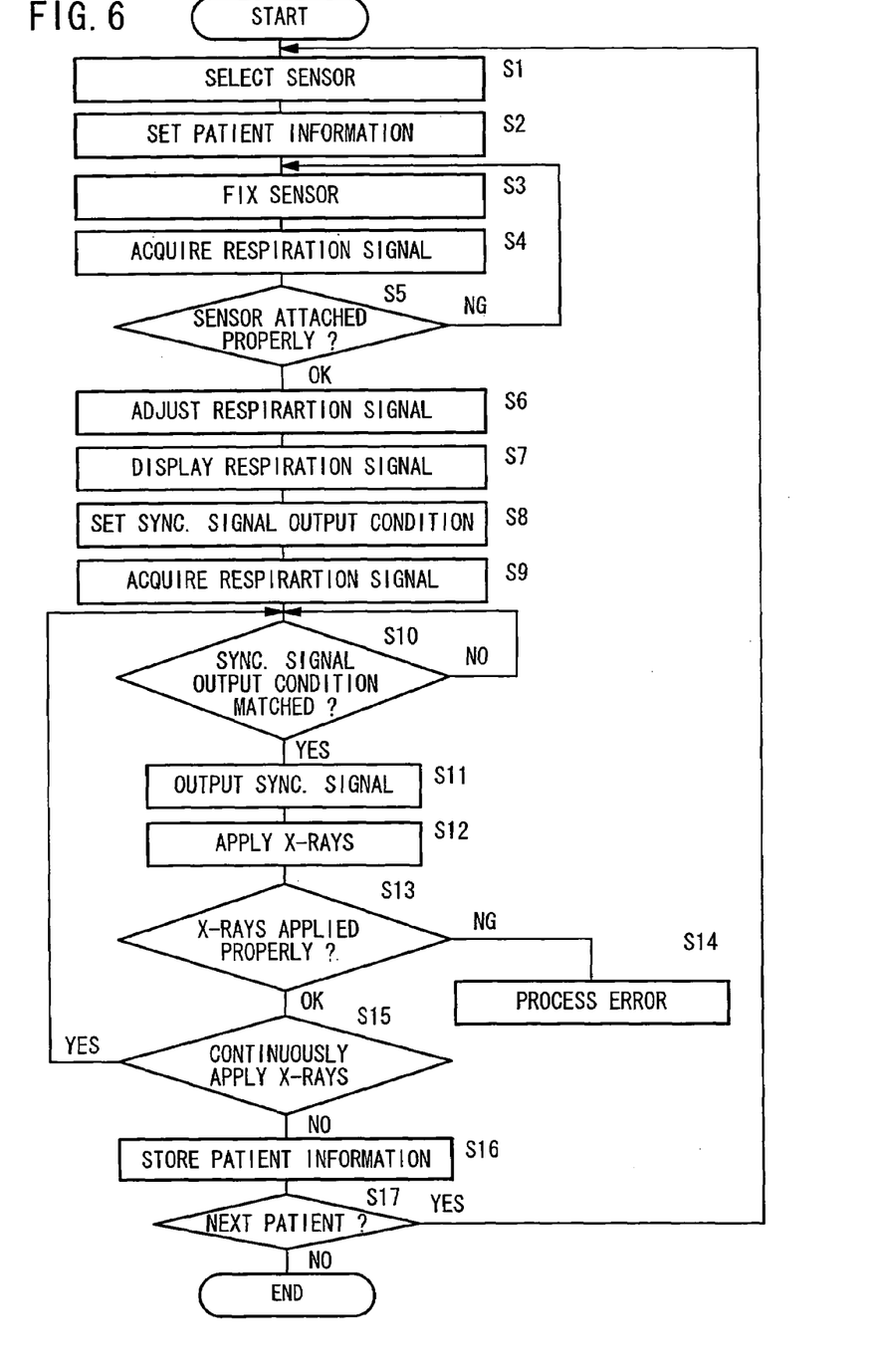
FIG. 6 is a flowchart of an operation sequence of the radiation image capturing system to which the radiation application synchronizing signal generating apparatus according to the embodiment of the present invention is applied.

With the examinee M placed on the bed 12, a sensor for acquiring a respiration signal of the examinee M is automatically selected in step S1. Specifically, the sensor connected state detector 54 of the sensor signal control device 32 detects a sensor connected to the sensor signal control device 32, and outputs a detected signal from the sensor to the sensor selector 56. When the sensor selector 56 detects a plurality of sensors connected to the sensor signal control device 32, the sensor selector 56 selects one of the sensors based on a preset priority order. For example, on the assumption that the priority order of the load cell 26 is the lowest, if the load cell 26 is connected full time to the sensor signal control device 32 and then the laser sensor 24 or the respiration control device 30 is connected to the sensor signal control device 32, then the sensor selector 56 selects the laser sensor 24 or the respiration control device 30. In this case, the laser sensor 24 or the respiration control device 30 can automatically be selected without the removal of the load cell 26.

The sensor selector 56 controls the sensor switcher 58 in order to supply a respiration signal from the selected sensor to the respiration signal converter 62, and indicates information as to which sensor has been selected on the selected sensor indicator 60. The information as to which sensor has been selected is supplied from the sensor signal control device 32 through the synchronizing signal output device 34 and the synchronizing signal output control device 36 to the input/output device 112 where the information is also displayed on the CRT.

After the sensor has been selected, patient information about the examinee M is set in the synchronizing signal output control device 36 in step S2. Patient information may be directly entered from the input/output device 112 or read from information stored in the data storage device 118.

The selected sensor is then fixed in position with respect to the examinee M in step S3. For example, if the laser sensor 24 is selected, then the laser sensor 24 is connected to the sensor signal control device 32, the distance between the laser sensor 24 and the examinee M is adjusted, and then selected sensor is fixed in position. If the respiration control device 30 is selected, then the respiration control device 30 is connected to the sensor signal control device 32, and the mask 28 is attached to the mouth of the examinee M. If the load cell 26 is selected, then the load cell 26 is connected to the sensor signal control device 32, and fastened to a region of the examinee M near the diaphragm or to an abdominal region by an adhesive tape or belt.

After the desired sensor is fixed to the examinee M, a respiration signal from the examinee M is acquired in step S4. If the laser sensor 24 has been selected, then a distance signal detected by the laser sensor 24 which represents the distance from the examinee M is amplified by the amplifier 48, and then supplied through the sensor switcher 58 to the respiration signal converter 62. The distance signal supplied to the respiration signal converter 62 is supplied to the sensor attached state determining unit 68, which compares the distance signal with a reference value to determine whether the laser sensor 24 is properly attached or not in step S5. The result is indicated by the sensor attached state indicator 70 as an energized state of the indicator lamps such as LEDs. If the result indicates that the distance between the laser sensor 24 and the examinee M is not in an allowable range, then the operator corrects the attached position of the laser sensor 24. If the load cell 26 has been selected, then a pressure signal detected by the load cell 26 is compared with a reference value to determine whether the load cell 26 is attached too strongly or too weakly. The result is indicated by the sensor attached state indicator 70. Based on the result, the operator can adjust the attached state of the load cell 26.

After the sensor has been properly fixed in position, the amplitude and offset of a respiration signal which may be a distance signal, a pressure signal, or an air flow rate signal supplied from the selected sensor are automatically adjusted in step S6.

The respiration signal from the laser sensor 24, the load cell 26, or the respiration control device 30 which has been selected by the sensor selector 56 is supplied through the sensor signal control device 32 and the synchronizing signal output device 34 to the synchronizing signal output control device 36. In the synchronizing signal output control device 36, the signal processor 100 calculates an adjustment signal, which is capable of standardizing the amplitude and offset of the respiration signal into optimum values irrespective of the respiratory state of the examinee M. The calculated adjustment signal, which comprises an amplitude adjustment signal and an offset adjustment signal, is supplied from the synchronizing signal output control device 36 through the synchronizing signal output device 34 to the sensor signal control device 32, where the adjustment signal is set in the respiration signal adjustor 66.

After the respiration signal is standardized using the adjustment signal by the signal processor 100 of the synchronizing signal output control device 36, the respiration signal is outputted from the signal processor 100 through the output controller 114 to the input/output device 112, which displays the waveform of the respiration signal on the CRT in step S7. The operator sets an output condition for a synchronizing signal based on the displayed waveform of the respiration signal in step S8.

The radiation image capturing system 10 according to the present embodiment allows output conditions shown in FIGS. 7 through 11 to be set selectively.

Figure 7:
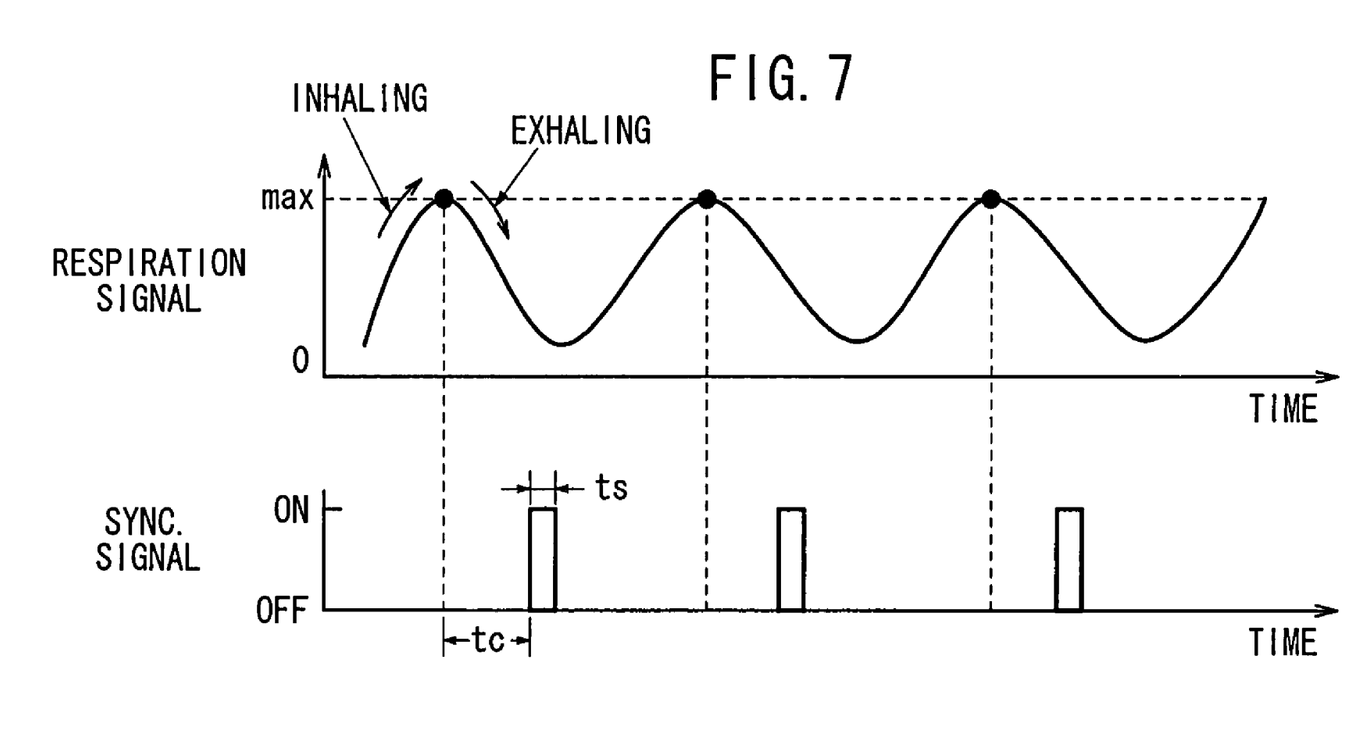
FIG. 7 is a diagram illustrative of an output condition for a synchronizing signal which is set in the radiation application synchronizing signal generating apparatus according to the embodiment of the present invention.
Figure 8:
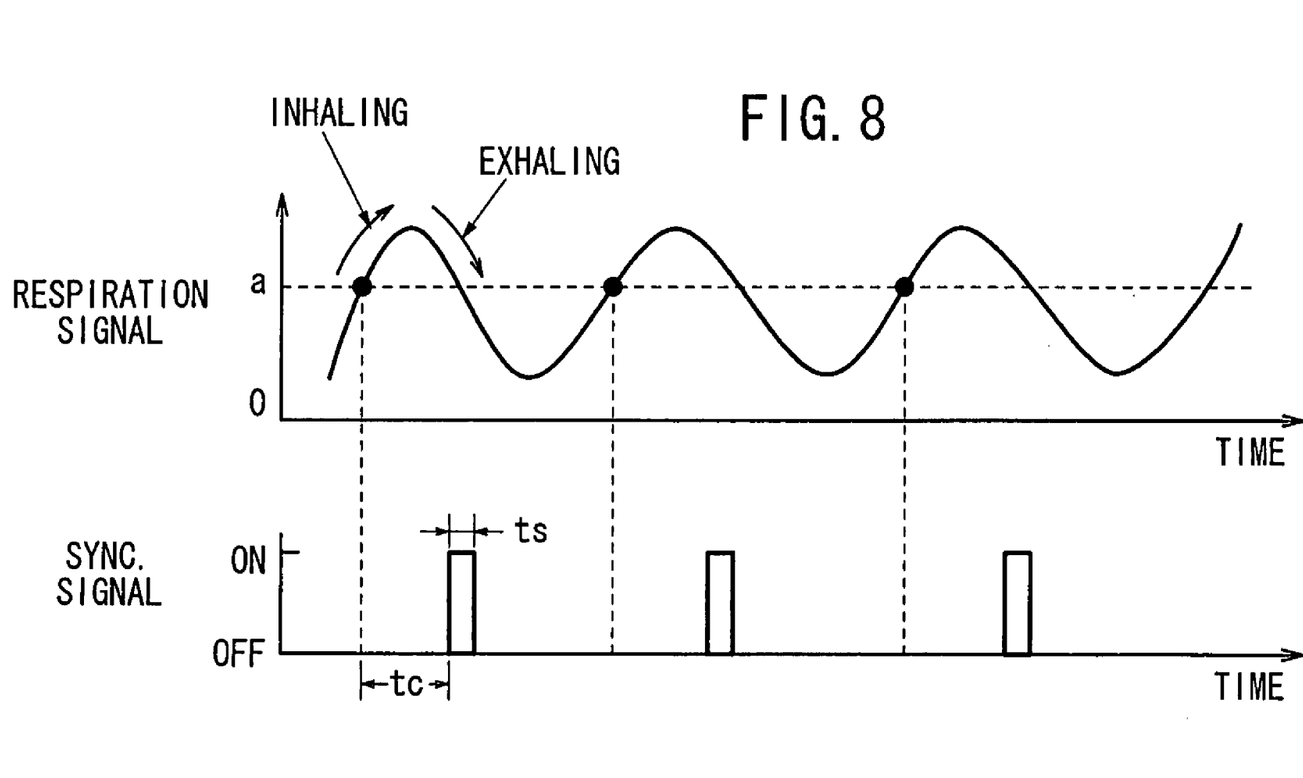
FIG. 8 is a diagram illustrative of an output condition for a synchronizing signal which is set in the radiation application synchronizing signal generating apparatus according to the embodiment of the present invention.
Figure 9:
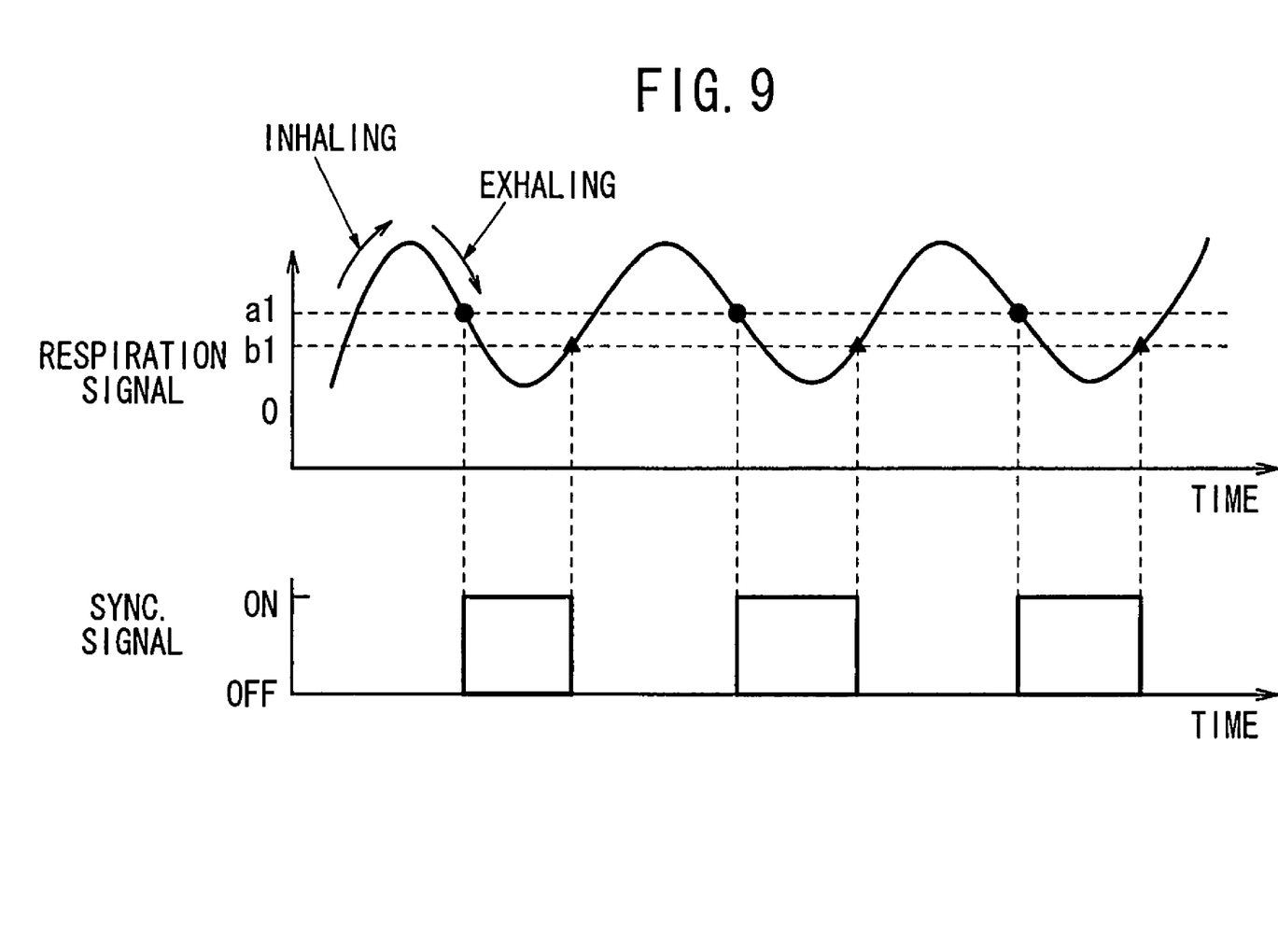
FIG. 9 is a diagram illustrative of an output condition for a synchronizing signal which is set in the radiation application synchronizing signal generating apparatus according to the embodiment of the present invention.
Figure 10:
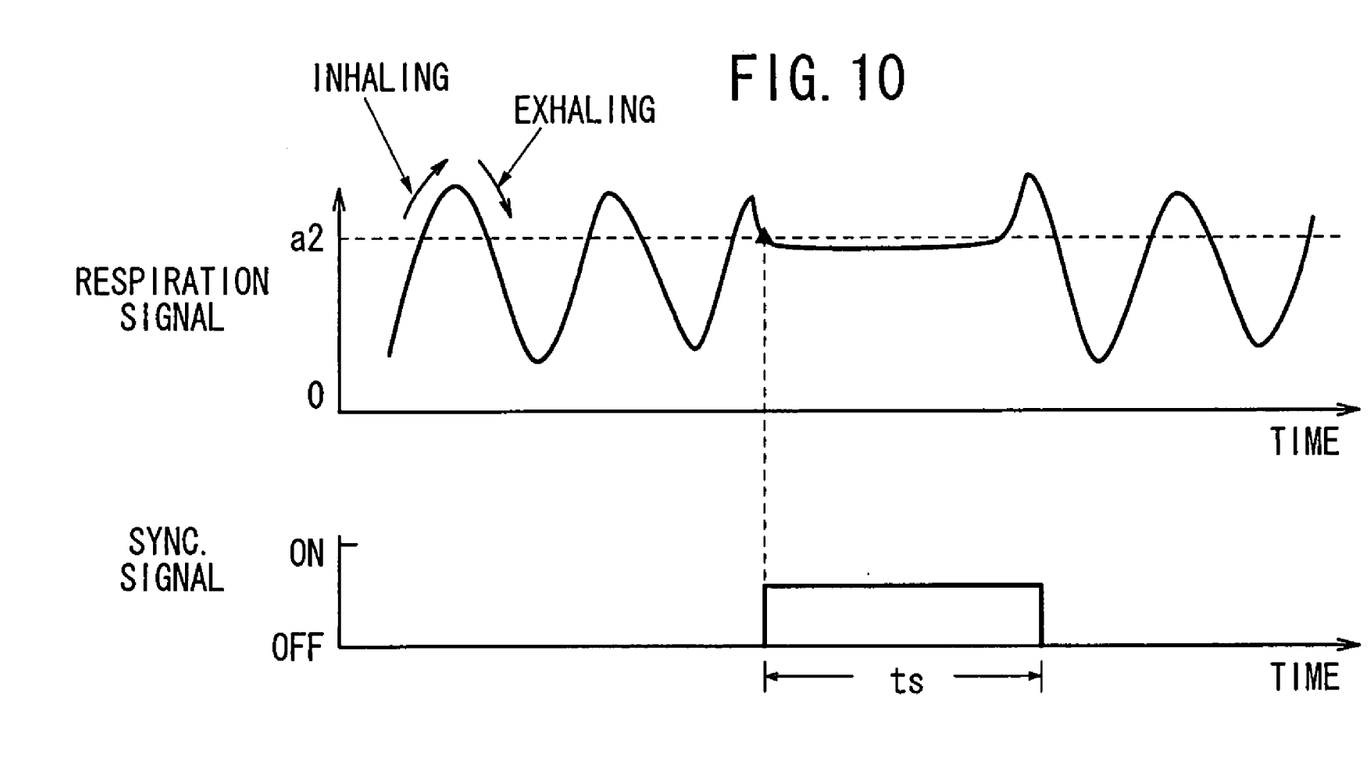
FIG. 10 is a diagram illustrative of an output condition for a synchronizing signal which is set in the radiation application synchronizing signal generating apparatus according to the embodiment of the present invention.
Figure 11:
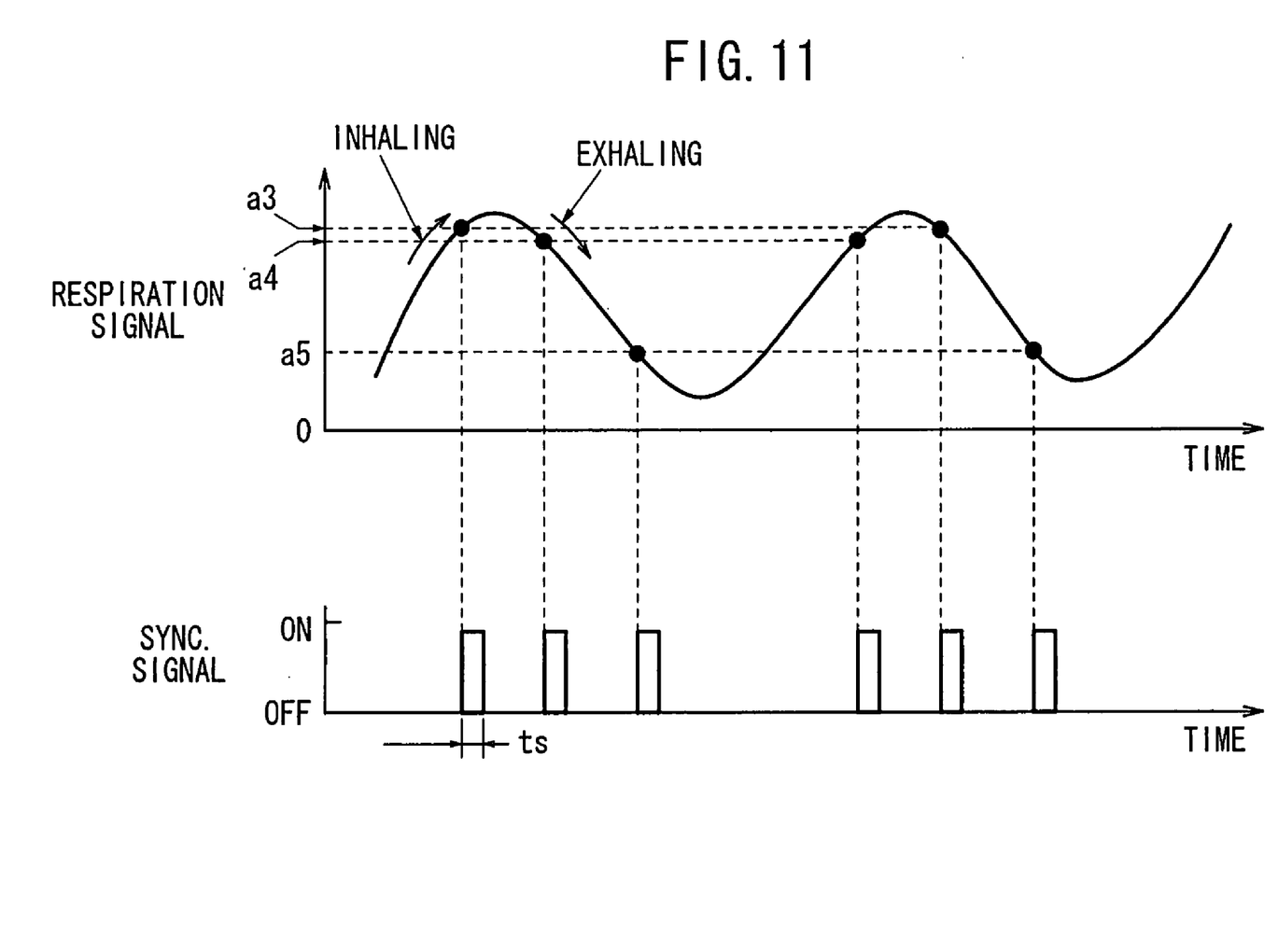
FIG. 11 is a diagram illustrative of an output condition for a synchronizing signal which is set in the radiation application synchronizing signal generating apparatus according to the embodiment of the present invention.

FIG. 7 shows an output condition for outputting a synchronizing signal for ts seconds after tc seconds from a peak amplitude max of the respiration signal. FIG. 8 shows an output condition for outputting a synchronizing signal for ts seconds after tc seconds from an arbitrary amplitude a in one respiratory cycle. FIG. 9 shows an output condition for outputting a synchronizing signal between two arbitrary amplitudes a1, b1 in one respiratory cycle. FIG. 10 shows an output condition for outputting a synchronizing signal for ts seconds from a forced stop on the respiration at an amplitude a2. FIG. 11 shows an output condition for outputting a synchronizing signal for ts seconds from each of arbitrary amplitudes a3, a4, a5 in one respiratory cycle. One of these output conditions can be selected depending on the examinee's region whose image is to be captured and the state of the examinee M, e.g., age, respiratory level.

When an output condition for a synchronizing signal is set, the synchronizing signal output control device 36 supplies setting data of the peak amplitude max or the amplitudes a, a1 through a5, b1, through the synchronizing signal output device 34 and the sensor signal control device 32 to the respiration monitor 38. The respiration monitor 38 controls the target respiration level indicator 40 to indicate the supplied setting data. The respiration monitor 38 also receives the respiration signal detected by the laser sensor 24 or the like from the sensor signal control device 32, and controls the respiration level indicator 42 to indicate the present respiratory level of the examinee M.

Therefore, the examinee M can recognize the relationship between its respiratory state and the timing to generate a synchronizing signal, allowing a more appropriate image capturing. If the output condition shown in FIG. 10 is set, then the examinee M can recognize its own respiratory state with respect to a forced breathing stop level indicated on the target respiration level indicator 40 of the respiration monitor 38, and hence can predict a period until the examinee M comes to a breathing stop. When breathing is to be stopped, the examinee M may be notified of such a stop by some kind of sound.

After an output condition for a synchronizing signal is set, the radiation image capturing system 10 starts capturing a radiation image of the examinee M.

A respiration signal detected by the laser sensor 24 or the like is amplified by the amplifiers 48, 50, 52 and supplied through the sensor switcher 58 to the respiration signal converter 62 in step S9. In the respiration signal converter 62, the amplitude and offset of the respiration signal are adjusted by the adjustment signal which has been set in the respiration signal adjustor 66. The adjusted respiration signal is supplied through the synchronizing signal output device 34 to the signal processor 100 of the synchronizing signal output control device 36, which compares the respiration signal with the set output condition for a synchronizing signal in step S10.

For example, if the output condition for a synchronizing signal has been set as shown in FIG. 7, then the signal processor 100 detects the peak amplitude max of the respiration signal and then outputs a synchronizing signal for ts seconds after tc seconds from the detected peak amplitude max in step S11.

The synchronizing signal generated by the signal processor 100 is supplied from the synchronizing signal output control device 36 to the synchronizing signal output device 34, and thereafter supplied from the synchronizing signal output unit 80 to the X-ray control device 11. When supplied with the synchronizing signal, the X-ray control device 11 outputs a shot signal to the high-voltage generating device 13. In response to the supplied shot, the high-voltage generating device 13 energizes the X-ray source 14 to apply X rays to the examinee M in step S12.

At the same time the high-voltage generating device 13 applies the high voltage to the X-ray source 14, the high-voltage generating device 13 generates an X-ray application signal and supplies the generated X-ray application signal through the sensor signal control device 32 to the signal processor 78 of the synchronizing signal output device 34. The signal processor 78 compares the supplied X-ray application signal with the synchronizing signal to check if the X-rays are properly applied to the examinee M or not, based on the synchronizing signal in step S13. If the signal processor 78 judges that the X-rays are not properly applied to the examinee M, then the signal processor 78 performs a predetermined error process by outputting the result to the X-ray control device 11 in step S14, and displays the error on the input/output device 112 via the synchronizing signal output control device 36.

If the output condition for a synchronizing signal has been set as shown in FIG. 7 and it is judged that the X-rays are properly applied to the examinee M based on the synchronizing signal, then the high-voltage generating device 13 continuously applies the X-rays to the examinee M while the synchronizing signal is being supplied continuously for the ts seconds in step S15.

The X-ray detector 16, which is located opposite of the examinee M from the X-ray source 14, detects X-rays that have passed through the examinee M and produces examinee-transmitted data. The examinee-transmitted data is collected by the data collecting device 18, and then transferred to the image reconstructing device 20, which reconstructs a tomographic image of the examinee M from the examinee-transmitted data. The reconstructed tomographic image is displayed on the image display device 22 for diagnosis.

When the reconstruction of the tomographic image is completed, the synchronizing signal output control device 36 stores the patient information including image capturing conditions in the data storage device 118 in step S16. Then, the synchronizing signal output control device 36 confirms whether or not there is a next patient or examinee in step S17. If there is none, then the operation sequence of the radiation image capturing system 10 is completed.

As described above, it is possible to obtain an appropriate radiation image irrespective of the respiratory state of the examinee M, based on an optimum synchronizing signal which is set depending on the state of the examinee M.

In the above embodiment, the period of time the X-rays are to be applied to the examinee M is set according to the output condition for a synchronizing signal. However, only the time to start applying X-rays to the examinee M may be controlled according to a synchronizing signal, and the period of time the X-rays are to be applied to the examinee M may be controlled by the X-ray control device 11.

The pattern of a respiration signal which has already been obtained may be stored as a predicted respiration pattern, and a respiration signal detected from the examinee M may be compared with the predicted respiration pattern. If the detected respiration signal does not fall within a predetermined range of the predicted respiration pattern, then it may be judged that the examinee M is in a state not suitable for image capturing, and the image capturing process may be interrupted. The predicted respiration pattern may be updated based on a detected respiration signal.

In the above embodiment, a radiation image of the examinee M is captured by applying X-rays to the examinee M. However, the principles of the present invention are also applicable to other systems in which other radiations are applied to the examinee M to capture a radiation image.

Although a certain preferred embodiment of the present invention has been shown and described in detail, it should be understood that various changes and modifications may be made therein without departing from the scope of the appended claims.

What is claimed is:

1. An apparatus for generating a synchronizing signal for applying radiation to a respiratory moving object, comprising:
  a moving state detector for detecting a respiration-induced moving state of the respiratory moving object and outputting a moving state signal representing the detected respiration-induced moving state;
  an output condition setting unit for setting an output condition for the synchronizing signal with respect to said moving state signal outputted from said moving state detector;
  a moving state signal determining unit for determining whether said moving state signal outputted from said moving state detector is in a predetermined relationship to said output condition or not; and
  a synchronizing signal generator for generating said synchronizing signal based on a result from said moving state signal determining unit,
  wherein said output condition setting unit enables said output condition for said synchronizing signal to be selectively set at one of a plurality of predefined output conditions, all of said predefined output conditions being made available for selection by said output condition setting unit, wherein, in at least one of said plurality of predefined output conditions, said synchronizing signal is generated and radiation is applied during continuous respiration and movement of said respiratory moving object, and wherein said plurality of output conditions include all of:

an output condition for outputting said synchronizing signal for a predetermined number of seconds (ts), after a predetermined number of seconds (tc) has elapsed from a peak amplitude (max) of the respiration signal;

an output condition for outputting said synchronizing signal for a predetermined number of seconds (ts), after a predetermined number of seconds (tc) has elapsed from an arbitrary amplitude (a) in the respiratory cycle;

an output condition for outputting said synchronizing signal between two arbitrary amplitudes (a1, b1) in the respiratory cycle;

an output condition for outputting said synchronizing signal for a predetermined number of seconds (ts) after a forced stop in respiration at an arbitrary amplitude (a2); and an output condition for outputting said synchronizing signal for a predetermined number of seconds (ts) after each of a plurality of arbitrary amplitudes (a3, a4, a5) in the respiratory cycle.

2. An apparatus according to claim 1, wherein a plurality of said moving state detectors are connectably provided, said apparatus further comprising:

a detector selector for selecting one of said moving state detectors according to a preset priority order.

3. An apparatus according to claim 2, further comprising:

a connected state detector for detecting a connected state of said moving state detector and outputting a signal representing the detected connected state to said detector selector.

4. An apparatus according to claim 1, further comprising:

a moving state indicator for concurrently indicating the level of a target moving state signal set by said moving state signal determining unit and the level of said moving state signal outputted from said moving state detector.

5. An apparatus according to claim 4, wherein said moving state indicator is disposed in a position which is perceptible by said respiratory moving object.

6. An apparatus according to claim 1, further comprising:

a moving state signal adjustor for adjusting the amplitude and offset of said moving state signal outputted from said moving state detector to standardize said moving state signal.

7. An apparatus according to claim 1, further comprising:

an applied state detector for detecting an applied state of said radiation based on said synchronizing signal and outputting an applied state signal representing the detected applied state; and an applied state determining unit for comparing the applied state signal outputted from said applied state detector with said synchronizing signal to determine whether said radiation is applied to said respiratory moving object according to said synchronizing signal or not.

8. An apparatus according to claim 1, further comprising:

a moving state controller for controlling the moving state of said respiratory moving object based on the result from said moving state signal determining unit before said synchronizing signal is generated.

9. An apparatus according to claim 1, further comprising:

a set state determining unit for determining a state in which said moving state detector is set on said respiratory moving object, based on said moving state signal outputted from said moving state detector.

10. An apparatus according to claim 1, wherein said moving state detector comprises a laser sensor for detecting a distance up to said respiratory moving object.

11. An apparatus according to claim 1, wherein said moving state detector comprises a load cell for detecting a pressure on a predetermined region of said respiratory moving object.

12. An apparatus according to claim 1, wherein said moving state detector comprises a flow rate sensor for detecting an air flow rate depending on the respiration of said respiratory moving object.

13. An apparatus for generating a synchronizing signal for applying radiation to a respiratory moving object, comprising:

a moving state detector for detecting a respiration-induced moving state of the respiratory moving object and outputting a moving state signal representing the detected respiration-induced moving state;

an output condition setting unit for setting an output condition for the synchronizing signal with respect to said moving state signal outputted from said moving state detector;

a moving state signal determining unit for determining whether said moving state signal outputted from said moving state detector is in a predetermined relationship to said output condition or not; and a synchronizing signal generator for generating said synchronizing signal based on a result from said moving state signal determining unit, wherein a plurality of said moving state detectors are connectably provided, said plurality of said moving state detectors including all of a laser sensor for detecting a distance up to said respiratory moving object, a load cell for detecting a pressure on a predetermined region of said respiratory moving object, and a flow rate sensor for detecting an air flow rate depending on the respiration of said respiratory moving object, said apparatus further comprising:

a detector selector for selecting one of said plurality of moving state detectors according to a preset priority order.

14. An apparatus according to claim 13, further comprising:

a connected state detector for detecting a connected state of said moving state detector and outputting a signal representing the detected connected state to said detector selector.

* * * * *